US00PP27896P3

(12) United States Plant Patent
Rayner

(10) Patent No.: US PP27,896 P3
(45) Date of Patent: Apr. 18, 2017

(54) MANGO TREE NAMED 'R10/8'

(50) Latin Name: *Mangifera indica*
Varietal Denomination: R10/8

(71) Applicant: Kenneth Rayner, Katherine (AU)

(72) Inventor: Kenneth Rayner, Katherine (AU)

( * ) Notice: Subject to any disclaimer, the term of this patent is extended or adjusted under 35 U.S.C. 154(b) by 53 days.

(21) Appl. No.: 14/544,812

(22) Filed: Feb. 19, 2015

(65) Prior Publication Data

US 2016/0249502 P1 Aug. 25, 2016

(51) Int. Cl.
*A01H 5/08* (2006.01)

(52) U.S. Cl.
USPC ..... Plt./159

(58) Field of Classification Search
USPC ..... Plt./156, 159
See application file for complete search history.

(56) References Cited

PUBLICATIONS

Plant Variety Journal: Offical Journal of Plant Breeder's Rights Office. vol. 24: 4. 2012. 12 pages.*

Mango Matters. 2014. vol. 15. retrieved on Nov. 30, 2016, retrieved from the Internet at (https://static1.squarespace.com/static/53b0ef57e4b04ed3debabc4f/t/53eb11d7e4b09c55b3b01711/1407914455144/Mango+Matters+Autumn+-+Final+%28Interactive%29.pdf). 3 pages.*

* cited by examiner

*Primary Examiner* — June Hwu
*Assistant Examiner* — Karen Redden
(74) *Attorney, Agent, or Firm* — Michelle Bos Legal LLC

(57) ABSTRACT

A new mango tree named 'R10/8', distinguished by its tendency to dwarfing and early maturing fruit.

3 Drawing Sheets

Genus and species: *Mangifera indica.*
Variety denomination: 'R10/8'.

CROSS-REFERENCE TO RELATED APPLICATIONS

None

BACKGROUND AND SUMMARY OF THE VARIETY

The new mango tree 'R10/8' originated as a controlled cross of 'Irwin' (female parent, not patented) and an unknown male parent, likely 'Kensington Pride' (not patented). The initial cross was made at Katherine, Northern Territory, Australia, and seedlings resulting from the cross were planted in the same location. 'R10/8' was selected from among the seedlings for further observation due to its distinctive fruit and its tendency to dwarfing. In 2001, 'R10/8' was asexually propagated by grafting at Katherine, Northern Territory, Australia and was field planted the next year. 'R10/8' has since been observed to reproduce true to type over successive asexually propagated generations.

'R10/8' is distinguishable from its parents and other known varieties by the following characteristics:

- 'R10/8' is poly-embryonic, as compared to 'Hayden' (not patented) and 'B74' ("Calypso", U.S. Plant Pat. No. 17,770) which are mono-embryonic.
- 'R10/8' is an early-maturing variety, as compared to 'Kensington Pride' which matures mid-season, and 'Honey Gold' (not patented) and 'Parvin' (not patented) which are late-maturing varieties.

- 'R10/8' is a smaller tree than female parent 'Irwin' with shorter internodes.

BRIEF DESCRIPTION OF THE PHOTOGRAPHS

Figure 1:
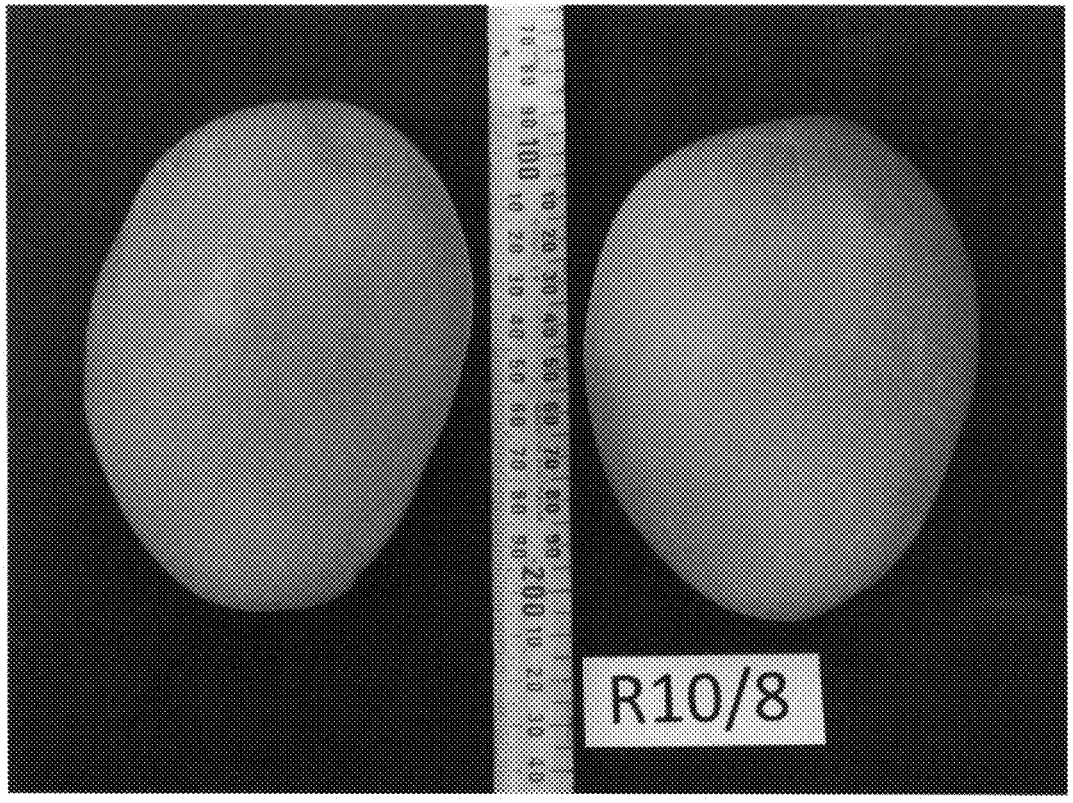
FIG. 1 shows edible ripe fruit of the 'R10/8' variety.
Figure 2:
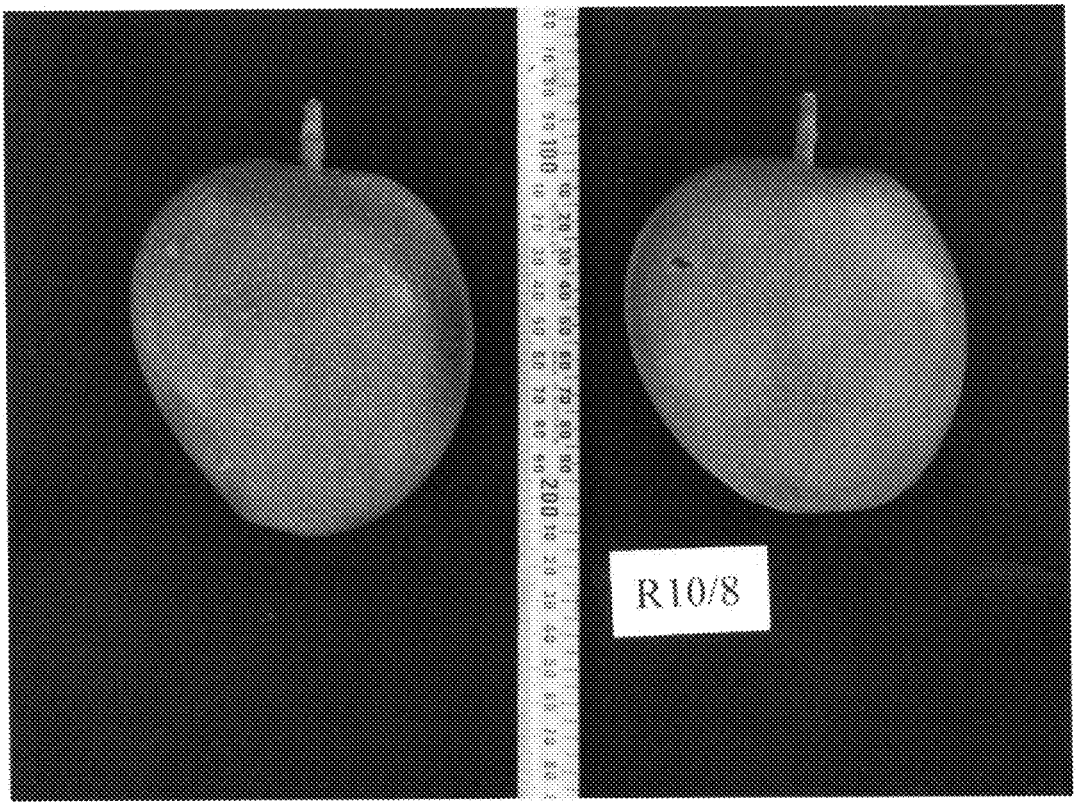
FIG. 2 shows mature fruit of the 'R10/8' variety, ready to pack and transport (about 1 month earlier than the fruit shown in FIG. 1); and, FIG. 3 shows a tree of the 'R10/8' variety (planted in 2002, photographed in 2012).
Figure 3:
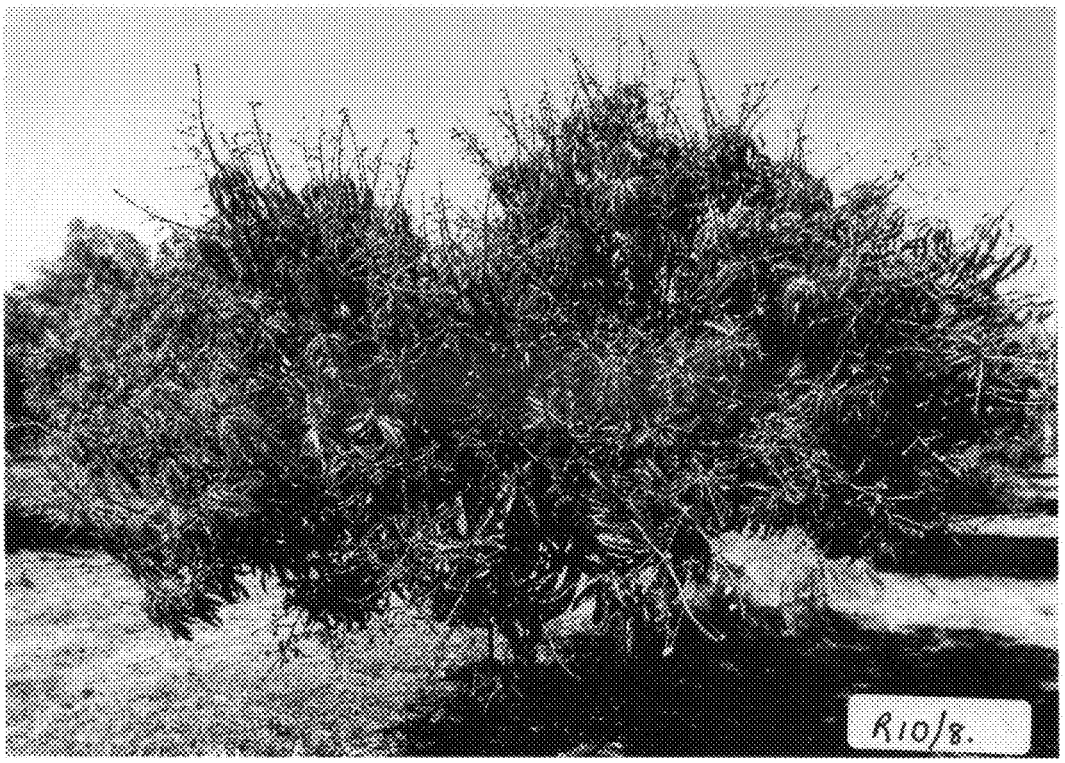

The colors of the claimed variety may vary with lighting conditions. Color characteristics of the variety should therefore be determined with reference to the observations described herein, rather than from these illustrations alone.

DETAILED BOTANICAL DESCRIPTION

The following detailed botanical description is based on observations recorded during the 2009 to 2012 growing seasons of three- to six-year-old trees planted in 2006 and grown on 'RH34' rootstock (not patented) at Berry Springs, Northern Territory, Australia. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants of the new variety may vary from the stated average. Colors are described with reference to The Royal Horticultural Society Mini Colour Chart (2007).

Tree:
*Vigor*.—Low vigor.
*Height*.—Small to medium, about 3.7 m.
*Spread*.—About 4.3 m.
*Growth habit*.—Spreading.
*Productivity*.—Heavy, regular bearer.
*Trunk diameter*.—20 cm at base.
*Bark texture*.—Moderately rough.
*Bark color*.—Mottled brown (greyed-orange) 165A.

Branches:
*Bark color*.—Greyed-orange 165A.
*Bark texture*.—Smooth.
*Diameter*.—13 cm to 16 cm (primary branches).

Inflorescence:
*Number of years to first flowering*.—3 years.
*Regularity of flowering*.—Every year.
*Bloom date*.—Approximately June 20 to July 20, varies by year.
Form.—Panicle.
*Inflorescence position*.—Apical.
*Axis growth habit*.—Semi-erect.
*Shape*.—Broadly pyramidal.
*Length*.—40 cm.
*Width*.—28 cm.
*Color*.—Red.
*Peduncle*.—Short. 10 mm.
*Peduncle color*.—Greyed-purple 185B.
*Pubescence*.—None.
*Presence of leafy bracts*.—None.
*Flower bud*.—Diameter 3 mm, yellow-green 152D, shape pyramidal.
*Density of flowers*.—Very dense, up to 2000 flowers per panicle.
*Type of flower*.—Pentamerous; male and hermaphrodite.
*Flower size*.—Diameter 5 mm to 10 mm.
*Fragrance*.—Pungent.
*Flower color*.—White 155A with yellow throat that turns pink with age, pubescent.
*Pedicel*.—Length 3 mm, red to brown in color.
*Stamen*.—Equal.
*Anther*.—Red; pollen is grey after dehiscence.
*Pollinator*.—Not required.

Leaves:
*Length*.—22 cm.
*Width*.—4.8 cm.
*Margin*.—Entire, undulate.
*Pubescence*.—None.
*Color*.—Young leaf Greyed-orange 172A.
*Color*.—Mature leaf Upper surface dark green 137A, lower surface 137C.
*Leaf shape*.—Lanceolate.
*Venation*.—Primary central vein with herringbone side veins.
*Apex shape*.—Acuminate.
*Base shape*.—Cuneate.
*Petiole length*.—4.8 cm.
*Petiole diameter*.—3 mm.
*Petiole color*.—Yellow-green 146C.
*Leaf orientation*.—Horizontal.
*Leaf arrangement*.—Spiral.

Fruit:
*Weight*.—350 g to 430 g.
*Length*.—115 mm.
*Diameter*.—85 mm.
*Apex*.—Rounded.
*Form of shoulder*.—Rising, then rounded outward.
*Stylar scar*.—Absent or small.
*Sinus*.—Absent.
*Form of stalk cavity*.—Shallow.
*Stalk attachment*.—Vertical.
*Stalk length*.—22 to 30 cm.
*Stalk diameter*.—Tapering from 8 mm to 4 mm.
*Stalk color*.—Yellow-green 144A.
*Beak*.—Present.
*Skin*.—Tough, thin.
*Skin color of immature fruit*.—Green 141C with red 166A blush when exposed to direct sunlight.
*Skin color of mature fruit*.—Bright yellow 14B with red 44A blush.
*Flesh texture*.—Coarse, very firm and juicy.
*Flesh color*.—Yellow 14A.
*Sweetness*.—14 Brix and higher.
*Fiber*.—Somewhat fibrous.
*Aroma*.—Mild.
*Fruit per panicle*.—1 to 3.

Stone:
*Length*.—7.6 cm.
*Width*.—4.4 cm.
*Depth*.—1.6 cm.
*Venation*.—Strong.
*Texture of stone fiber*.—Soft.
*Adherence of fiber to stone*.—Strong.
*Color*.—White 155A.
*Embryony*.—Poly-embryonic.
*Storage*.—Stores for about 12 days at ambient temperature.
*Susceptibility to bruising*.—Slight.
*Susceptibility to wind*.—None.
*Relative harvest maturity*.—Early; Oct. 1 to Oct. 20, 2016, varies by year.
*Use*.—Fresh market.
*Drought, heat and cold tolerance*.—Tolerant in area grown (Berry Springs, Northern Territory, Australia).

I claim:

1. A new and distinct variety of mango tree, substantially as illustrated and described herein.

* * * * *